(12) United States Patent
Schleifer

(10) Patent No.: US 7,351,379 B2
(45) Date of Patent: *Apr. 1, 2008

(54) FLUID CONTAINMENT STRUCTURE

(75) Inventor: Arthur Schleifer, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 415 days.

This patent is subject to a terminal disclaimer.

(21) Appl. No.: 10/172,887

(22) Filed: Jun. 14, 2002

(65) Prior Publication Data

US 2003/0231983 A1 Dec. 18, 2003

(51) Int. Cl.
*B01L 3/00* (2006.01)
*G01N 1/28* (2006.01)

(52) U.S. Cl. .................. 422/102; 422/50; 422/68.1; 422/99; 435/287.1; 435/288.3; 435/288.4; 264/494

(58) Field of Classification Search .................. 422/99, 422/102, 104, 939, 50, 68.1; 435/283.1, 435/287.1, 288.3, 288.4, 305.4; 359/398; 264/494
See application file for complete search history.

(56) References Cited

U.S. PATENT DOCUMENTS

| | | | | |
|---|---|---|---|---|
| 4,447,140 A | * | 5/1984 | Campbell et al. ........... 359/396 |
| 5,346,672 A | * | 9/1994 | Stapleton et al. ........... 422/102 |
| 5,939,251 A | * | 8/1999 | Hu ................................. 435/4 |
| 5,948,685 A | * | 9/1999 | Angros ........................ 436/63 |
| 6,180,314 B1 | * | 1/2001 | Berndt ....................... 430/180 |
| 6,399,394 B1 | * | 6/2002 | Dahm et al. ................ 436/180 |
| 6,485,918 B1 | * | 11/2002 | Schermer et al. .............. 435/6 |
| 6,545,758 B1 | * | 4/2003 | Sandstrom ................... 356/317 |
| 6,818,395 B1 | * | 11/2004 | Quake et al. ................... 435/6 |
| 2003/0219890 A1 | * | 11/2003 | Gordon et al. .......... 438/287.2 |
| 2005/0106617 A1 | * | 5/2005 | Besemer et al. ............... 435/6 |
| 2005/0112757 A1 | * | 5/2005 | Spence et al. .......... 435/287.2 |

OTHER PUBLICATIONS

Hawley, G. The Condensed Chemical Dictionary, tenth edition, 1981, pp. 20-21.*

* cited by examiner

*Primary Examiner*—Maureen M. Wallenhorst

(57) ABSTRACT

A fluid containment structure that includes a substrate with a gasket surface and a form-in-place gasket disposed on the gasket surface and a method for forming the fluid containment structure are described. The form-in-place gasket is disposed around and marks the perimeter of an interior area on the substrate. The interior area and the form-in-place gasket define a well that is adapted for retaining a fluid. The fluid containment structure may be associated with or form a portion of an analysis site where a sample fluid retained in the fluid containment structure may be analyzed.

24 Claims, 4 Drawing Sheets

னnot # FLUID CONTAINMENT STRUCTURE

FIELD OF THE INVENTION

The invention relates generally to manufacture of biochemical assays. More specifically, this invention relates to formation of fluid-tight seals and containment structures relating to biological assays.

BACKGROUND OF THE INVENTION

Biomolecular arrays (such as DNA or RNA arrays) are known and are used, for example, as diagnostic or screening tools. Such arrays include regions of usually different sequence biomolecules (such as polynucleotides or polypeptides) arranged in a predetermined configuration on a substrate. These regions (sometimes referenced as "array features") are positioned at respective locations ("addresses") on the substrate. Biomolecular arrays typically are fabricated on planar substrates either by depositing previously obtained biomolecules onto the substrate in a site specific fashion or by site specific in situ synthesis of the biomolecules upon the substrate. The arrays, when exposed to a sample, will undergo a binding reaction with the sample and exhibit an observed binding pattern. This binding pattern can be detected upon interrogating the array. For example all biomolecule targets (for example, DNA) in the sample can be labeled with a suitable label (such as a fluorescent compound), and the label then can be accurately observed (such as by observing the fluorescence pattern) on the array after exposure of the array to the sample. Assuming that the different biomolecule targets were correctly deposited in accordance with the predetermined configuration, then the observed binding pattern will be indicative of the presence and/or concentration of one or more components of the sample.

In use, the surface of the array is contacted with a solution containing the sample. The speed and specificity of the binding reaction is dependent on several factors, including composition of the solution (ionic strength, pH, polarity, concentration and identity of the sample), temperature, and speed of mixing of the sample. Samples tend to be expensive, precious, or limited to very small quantities. Therefore, current methods seek to reduce the amount of sample required by reducing the amount of sample solution needed to contact the array. One current method accomplishes this by confining the solution under a coverslip placed on top of the array, creating a thin layer of solution between the array surface and the coverslip. While this technique minimizes the quantity of solution required to contact the U.S. Pat. No.array, it eliminates the ability to mix or stir the solution while the array is being exposed to the solution. Mixing is thus limited to diffusion of the sample molecules within the thin layer of solution between the coverslip and the array surface. This results in very long incubation time, typically, over night and up to 24 hours. The coverslip method also does not allow one to seal the system (undesirable, because it allows evaporation at the edges to occur). The coverslip method frequently results in spatially non-uniform binding because of variations in the flatness of the glass, the bending of the glass, and the thickness of the thin layer of solution. The coverslip method is also messy and clumsy to use; during the disassembly process, it is easy to scratch the array since the glass cover is in close contact to the array substrate.

As an alternative, some array manufacturers have created packages for their arrays. In one type of package, the array substrate is glued in place and the package has a sealed inlet and outlet for the liquid sample. These packages usually have a relatively large (compared to the coverslip systems) distance between the array surface and the mating opposite surface used to seal the chamber. This allows the sample solution to flow across the array when injected into the package. The package usually has to be oriented so that the array surface is vertical to allow the leading air bubble to float to the top and out. The sample volumes in these packages are much larger than the coverslip method, typically greater than 100 microliters and up to 500 microliters or more.

Another technique to create an assay chamber for an array is to place a gasket between the array surface and a mating opposite surface and clamp with an external force. The distance between the two surfaces is typically between 0.5 mm and 1.0 mm. This distance is required to allow the sample solution to flow in the chamber without being restricted by capillary forces. An array enclosed in a package having an assay chamber is easier to handle and less likely to be damaged during use because the mating surface is kept at a distance from the array surface. Mixing of the sample solution across the array surface is possible in the assay chamber by either pumping the liquid sample back and forth across the array or rotating the package to move the liquid position within the sealed chamber. The problem with these types of chambers is the large volume of liquid sample required to fill the volume between the two surfaces while covering the array area. Large sample volumes are sometimes not possible or require dilution of the sample to fill the volume. Dilution of the sample reduces sensitivity of the measurement and may extend the incubation time.

Ideally, one would like to approach the small volumes of the coverslip method while allowing for a more protected sealed system. One such system is described in U.S. Pat. No. 6,361,486 to Gordon and U.S. Pat. No. 6,309,875 to Gordon. This technique uses variable orientation centrifugation to move the sample in a thin cross section between the array surface and the back plate. This technique uses centrifugation of the assay chamber to overcome capillary forces that deter mixing of the sample solution. By changing the orientation of the array during the centrifugation, the sample is moved across the array and allowed to mix during incubation. This system requires a reliable seal between the array surface and the back plate that is sufficiently thin to allow small volumes of sample to cover large areas of the array.

To form a good seal, typically a compliant material is compressed between the two surfaces. It is difficult to find compliant material that is sufficiently thin and compatible with the chemistry used for these biochemical experiments. Normal rubber sheet material is much thicker than what is required for this application. To reduce the volume of sample, a gasket thickness of 0.001" to 0.003" is required. Sheet materials typically become too flimsy or are relatively difficult to manipulate at such a small scale. One available material is thin sheets (down to 0.002") of silicone rubber. This material can be cut into the desired shape and placed on the array surface. A back plate is then carefully set in place, and pressure is applied to seal the assay chamber. In practice, this works, but the gasket is delicate, difficult to handle, and hard to keep in place while assembling the apparatus. Adhesives can be applied to one side of the silicone sheet. This allows the thin sheet of silicone rubber to be applied to the back plate and cut to the desired shape. Unwanted areas of the sheet are then peeled away. The sheet of silicone rubber can also be die cut to form the gasket before it is applied to the back plate. This is a difficult process. The adhesive adds to the thickness of the gasket and has to be compatible with all the chemicals that might be used in the biochemical assay. The silicone sheet material that forms the gasket must be wide enough (on the order of 1+millimeters) to provide strength and structural integrity to survive the process of applying the material to the plate. Therefore, while creating a chamber on the order of about 0.002" thick is possible using thin silicone sheet material, it is inconvenient and results in relatively wide strips of sheet material on the surface of the back plate (or, alternatively, the surface of the substrate).

There is thus a need for an array system allowing the use of relatively small amounts of sample solution while allowing the sample solution to be mixed or moved across the surface of the array to speed the binding reaction. Such an array system needs to have an assay chamber that is fluid tight to allow the sample solution to flow across the surface of the array and to be mixed without leaking.

SUMMARY OF THE INVENTION

The invention is thus addressed to the aforementioned deficiencies in the art, and provides novel methods for making a fluid-tight seal around an array to provide an assay chamber for containing the sample solution during the binding reaction.

More generally, the invention provides a form-in-place gasket on a gasket surface on a substrate as well as a method of making the form-in-place gasket on the gasket surface. The form-in-place gasket comprises a suitable gasket material that is deposited onto the gasket surface at the site where the finished gasket is desired, typically adjacent to an analysis site, e.g. site of a biochemical assay. For embodiments in which the desired gasket is relatively thin, the gasket material is selected to be a self-leveling, low viscosity, fluid material that is essentially inert to the conditions under which the analysis (such as a biochemical assay) is conducted. The method of making the form-in-place gasket includes depositing the gasket material in a predetermined configuration at the desired site on the gasket surface, and then curing the gasket material to form the form-in-place gasket. A cover having a mating surface that is complementary to the gasket surface can be disposed against the gasket, forming a fluid tight seal. With the cover in place, the substrate, the cover, and the form-in-place gasket define an assay chamber, typically associated with the analysis site.

The invention thus also provides for a fluid containment structure. The fluid containment structure includes a substrate that has a gasket surface with a form-in-place gasket on the gasket surface. The form-in-place gasket is disposed around and marks the perimeter of an interior area on the substrate. The interior area and the form-in-place gasket define a well that is adapted for retaining a fluid. The shape of the interior area may be altered depending on the desired use by altering the configuration of the form-in-place gasket. The fluid containment structure may be associated with or form a portion of an analysis site where a sample fluid retained in the fluid containment structure may be analyzed. The analysis site typically includes at least one analysis component (e.g. an array of immobilized oligonucleotides) necessary for performing, e.g. a biochemical assay, such as a binding reaction between an immobilized oligonucleotide and a complementary oligonucleotide in the sample solution.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein.

To facilitate understanding, identical reference numerals have been used, where practical, to designate corresponding elements that are common to the Figures. Figure components are not drawn to scale.

DETAILED DESCRIPTION

Figure 1:
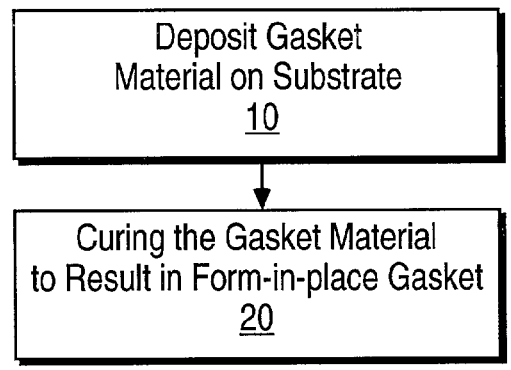
FIG. 1 is a flow chart describing a method according to the present invention.

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. In this specification and in the claims that follow, reference will be made to a number of terms that shall be defined to have the following meanings unless a contrary intention is apparent:

A form-in-place gasket, as the term is used herein, refers to a gasket which is formed on a gasket surface in a process that involves depositing a gasket material onto the gasket surface. The term "form-in-place gasket" also encompasses a plurality of discontinuous portions of gasket disposed on a surface, such as when formed by depositing gasket material on the surface discontinuously and then curing the gasket material. The gasket surface is the surface upon which the gasket is formed (or is intended to be formed). The mating surface is the surface that is complementary to the gasket surface and is disposed against the gasket formed on the gasket surface (or is intended to be disposed against the gasket formed on the gasket surface). Gasket material references a fluid material having properties that render the fluid material suitable for formation of a gasket. As used below, "gasket" typically references a form-in-place gasket according to the present invention, unless the context clearly indicates otherwise. "Fluid tight" when used to describe a seal, a chamber, or other feature references an ability to resist flow of a fluid past an intended boundary (typically defined by a gasket), but yet permits fluid flow within intended boundaries, such as on one side of a seal, into or out of a chamber via a port, or along the length of a channel. "Mixing feature" references structures formed on a surface (e.g. by depositing gasket material on the surface) that, due to the geometry or physical configuration of the structure, serves to aid mixing of the contents of a chamber. In certain embodiments, a "substrate" may include materials that are homogenous, heterogenous, or otherwise, and may include individual component parts that are combined to produce the substrate. Similarly, in certain embodiments, a "cover" may include materials that are homogenous, heterogenous, or otherwise, and may include individual component parts that are combined to produce the cover. "Substantially defined", as it relates to a substrate, a cover, and gasket "substantially defining" an assay chamber, means that the chamber need not be totally enclosed (e.g. the chamber may have one or more ports, or orifices), and/or that other elements (other than the substrate, cover, and gasket) may define a portion (e.g. less than about 20% of the surface area defining the assay chamber) of the assay chamber or may contribute (e.g. up to about 20% of the surface area defining the assay chamber) to defining the assay chamber. "Substantially" in other contexts means generally at least about 80% of the property or state referred to, unless the context clearly dictates otherwise. "Pliable" references a property of a material which is pliant or compressible. "Self-leveling" references a property of a material which tends to have a certain given thickness under a given set of conditions, and in particular references the property of certain gasket materials to flow, or to "slump", (after being deposited on a gasket surface but prior to completion of curing) to a certain thickness, where the thickness depends on properties of the gasket material applied and the conditions of application, including the conditions used for curing the gasket material and the properties of the surface on which the gasket material is deposited. "Non-slumping" references a property of a material which does not flow, or which maintains an essentially constant conformation, after being deposited on a gasket surface but prior to completion of curing. Of course, non-slumping materials may be manipulated to result in a changed conformation after being deposited on a gasket surface but prior to completion of curing, e.g. by being squeezed between a substrate and a cover, and this does not alter their "nonslumping" property. "Uniform thickness" describes gaskets or gasket materials applied to a surface such that substantially the entire gasket or applied gasket material has a given thickness (plus or minus about 20%), wherein the thickness of the gasket measured at various points varies by less than 20% of the given thickness of the gasket.

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide" refers to a sub-unit of a nucleic acid (whether DNA or RNA or analogue thereof) which includes a phosphate group, a sugar group and a nitrogen containing base, as well as analogs of such sub-units. A "nucleoside" references a nucleic acid subunit including a sugar group and a nitrogen containing base. A "nucleoside moiety" refers to a molecule having a sugar group and a nitrogen containing base (as in a nucleoside) as a portion of a larger molecule, such as in a polynucleotide, oligonucleotide, or nucleoside phosphoramidite. A "nucleotide monomer" refers to a molecule which is not incorporated in a larger oligo- or polynucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected. An "oligonucleotide" generally refers to a nucleotide multimer of about 2 to 100 nucleotides in length, while a "polynucleotide" includes a nucleotide multimer having any number of nucleotides. It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may comprise a phospho or phosphite group, and may include linkages where one or more oxygen atoms of the phospho or phosphite group are either modified with a substituent or replaced with another atom, e.g. a sulfur atom, or the nitrogen atom of a mono- or di-alkyl amino group. Such words as "bond," "bound," "binds," or "binding," may be used to express various modes of chemical binding, including covalent, ionic, hydrogen bonding, hydrophobic bonding, or mixed mode binding (combinations of the above); context may dictate when a specific meaning is permissible or required.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ϵ-nicotinoyl-lysine, isonipecotic acid, tetrahydroisoquinoleic acid, aaminoisobutyric acid, sarcosine, citrulline, cysteic acid, t-butylglycine, t-butylalanine, phenylglycine, cyclohexylalanine, β-alanine, 4-aminobutyric acid, and the like. An "oligopeptide" is a molecule containing from 2 to about 100 amino acid subunits. "Polypeptide" refers to a molecule having any number of amino acid subunits. "Biomolecule" refers to molecules generally derivable from living organisms, or analogues thereof. Biomolecules include, e.g. amino acids, oligopeptides, polypeptides, glycoproteins, nucleotide monomers, oligonucleotides, polynucleotides, saccharides, polysaccharides, hormones, growth factors, peptidoglycans, or the like. The term "biomolecular fluid" refers to any fluid that comprises biological fluids, biomolecules, and/or other biological substances or materials. Some examples of biological fluids include blood, plasma, serum, solutions containing proteins or nucleic acids, urine, cerebral spinal fluid, saliva, enzymatic mixtures substances and other related substances and fluids that are well known in the analytical and biomedical art.

The term "analysis site" refers to a location in a device where there is any use, singly or in combination, of chemical test reagents and methods, electrical test circuits and methods, physical test components and methods, optical test components and methods, and biological test reagents and methods to yield information about an analyte, e.g. a biomolecular fluid or other substance to be analyzed. Such methods are well known in the art and may be based on teachings of, e.g. Tietz Textbook of Clinical Chemistry, 3d Ed., Sec. V, pp. 776-78 (Burtis & Ashwood, Eds., W.B. Saunders Company, Philadelphia, 1999); U.S. Pat. No. 5,997,817 to Chrismore et al. (Dec. 7, 1999); U.S. Pat. No. 5,059,394 to Phillips et al. (Oct. 22, 1991); U.S. Pat. No. 5,001,054 to Wagner et al. (Mar. 19, 1991); and U.S. Pat. No. 4,392,933 to Nakamura et al. (Jul. 12, 1983), the teachings of which are hereby incorporated by reference, as well as others. Analysis sites may include detectors that test electrochemical properties of the biomolecular fluid (e.g. conductivity), or they may include optical means for sensing optical properties of the biomolecular fluid (e.g. chemiluminescence, fluorescence, or dye activation vie enzymatic action), or they may include biochemical reagents (e.g. antibodies, substrates, or enzymes) to sense properties (e.g. presence of antigens, clotting time, or clot lysis) of the biomolecular fluid. The analysis site may comprise biosensing or reagent material that will react with an analyte (e.g. glucose) in the biomolecular fluid so that information about the analyte may be obtained. An analysis site may include one or more bioarrays or a portion of a bioarray. "Analysis component" references any reagent, circuit, component, detector, means, or the like mentioned in this paragraph in relation to an analysis site, wherein the analysis component is in operable relation to other elements of the analysis site, and may include biomolecules deposited in a bioarray on a substrate. An analysis site may be, e.g. disposed adjacent to a substrate or in operable relation to an array chamber or a portion of an array chamber, and an analysis component may be in operable relation to a substrate.

An "array", unless a contrary intention appears, includes any one, two or three dimensional arrangement of addressable regions bearing a particular chemical moiety or moieties (for example, polynucleotide sequences) associated with that region. A "bioarray" is an array of biomolecules. An array is "addressable" in that it has multiple regions of different moieties (for example, different polynucleotide sequences) such that a region (a "array feature" or "spot" of the array) at a particular predetermined location (an "address") on the array will detect a particular target or class of targets (although an array feature may incidentally detect non-targets of that array feature). In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). While probes and targets of the present invention will typically be single-stranded, this is not essential. A "target solution" references a mobile phase comprising the target. "Interrogating" the array refers to obtaining information from the array, especially information about targets binding to the array. An "array format" refers to one or more characteristics of the array, such as array feature position, array feature size, or some indication of a moiety at a given location. "Hybridization assay" references a process of contacting a bioarray with a mobile phase containing target moieties. Further disclosure of form-in-place gaskets, particularly as related to array formats may be found in three applications co-filed with this application, titled "Form in Place Gaskets for Assays" (Schleifer), "Improved Hybridization Process for Bioarrays" (Schleifer and Ostrowski), "Multiple Array Format for Automation" (Schleifer and Caren), each of which is hereby incorporated by reference in its entirety.

The present invention provides a method of making a form-in-place gasket. Referring to FIG. 1, the method comprises first depositing a suitable gasket material onto a substrate 10 and then curing the gasket material on the substrate 20 to produce the form-in-place gasket. The gasket material is applied to the substrate in a predetermined configuration to provide for a form-in-place gasket having a desired configuration. The desired properties of the final form-in-place gasket, for example the spatial conformation of the gasket on the surface of the substrate, the desired dimensions and structural features of the gasket, and so on, will dictate the predetermined configuration. The gasket material is applied to the gasket surface so as to result in the final gasket having the desired configuration, for example to provide desired structural features such as conduits, chambers, mixing features, outlets and/or inlets when a cover is placed against the form-in-place gasket on the substrate.

A fluid containment structure may be formed that includes a substrate that has a gasket surface with a form-in-place gasket disposed on the gasket surface. In the fluid containment structure, the form-in-place gasket is disposed around and marks the perimeter of an interior area on the substrate. The interior area and the form-in-place gasket define a well that is adapted for retaining a fluid. The shape of the interior area may be altered depending on the desired use by altering the configuration of the form-in-place gasket. The fluid containment structure may be associated with or form a portion of an analysis site where a sample fluid retained in the fluid containment structure may be analyzed. The analysis site typically includes at least one analysis component (e.g. an array of immobilized oligonucleotides) necessary for performing, e.g. a biochemical assay, such as a binding reaction between an immobilized oligonucleotide and a complementary oligonucleotide in the sample solution.

Figure 2A:
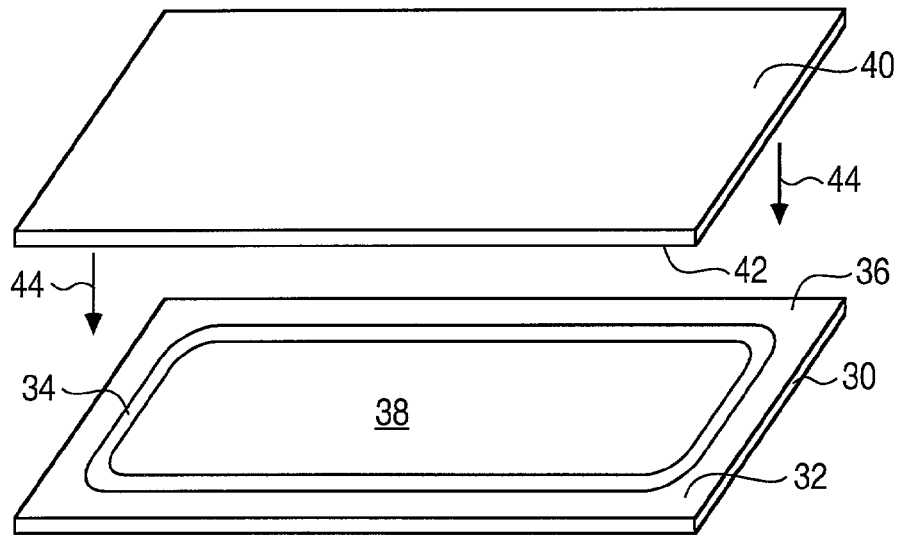
FIG. 2A illustrates a substrate, a form-in-place gasket, and a cover.

The gasket material may be deposited on a gasket surface in a variety of predetermined configurations, including a bead of gasket material deposited around the perimeter of a substrate to provide for a fluid-tight seal when a cover is placed on the gasket. The desired configuration may include, for example, a simple bead of gasket material surrounding the perimeter of an assay chamber, as well as more complex structures. Referring now to FIG. 2, FIG. 2A shows a substrate 30 having a gasket surface 32 with a form-in-place gasket 34 formed thereupon. The gasket surface 32 is that part of the substrate surface 36 on which the gasket material is deposited. The form-in-place gasket 34 comprises a simple bead of cured gasket material around the perimeter of an interior area 38 of the substrate surface 36 defined by the form-in-place gasket 34. A cover 40 having a mating surface 42 is adapted to be positioned in close proximity to the substrate 30, as indicated by arrows 44. The mating surface 42 is that part of the cover 40 which lies adjacent the form-in-place gasket 34 when the cover 40 is disposed adjacent the substrate 30. The mating surface 42 is complementary to the gasket surface 32 and is preferably smooth where it contacts the form-in-place gasket 34. The cover 40 is adapted to provide a tight seal by pressing the form-in-place gasket 34 between the gasket surface 32 and the mating surface 42. The gasket surface and the mating surface are each preferably planar, but in other embodiments may deviate from planar, e.g. portions of the gasket surface and mating surface may turn downward or upward (i.e. in the direction of the arrows 44 or in the reverse direction), so long as the gasket surface and mating surface are complementary, or substantially parallel (meaning substantially equidistant from each other along their length) when the cover is in place on the substrate, so that a tight seal may be formed. With the cover in place (in close proximity ("adjacent") to the substrate), the substrate, the cover, and the form-in-place gasket define an assay chamber. In the absence of the cover, substrate 30 and form-in-place gasket 34 provide a fluid containment structure, as illustrated in FIG. 2A.

The substrates shown in FIGS. 2A-2D are planar, but in alternate embodiments the substrate may have more complex structure, e.g. including one or more of recessed structures, elevated structures, channels, orifices, guides. For example, the interior area 38 of the substrate surface 36 defined by the form-in-place gasket 34 may have a recess in fluid communication with a channel formed in the interior area 38 of the substrate surface 36, the channel leading through an orifice to an external fluid supply source, allowing, e.g. rinsing of the interior surface during use, with a separate orifice serving as a drain. Such orifices may variously be referred to as ports, inlets, outlets, drains, vents, or such similar terms.

Figure 2B:
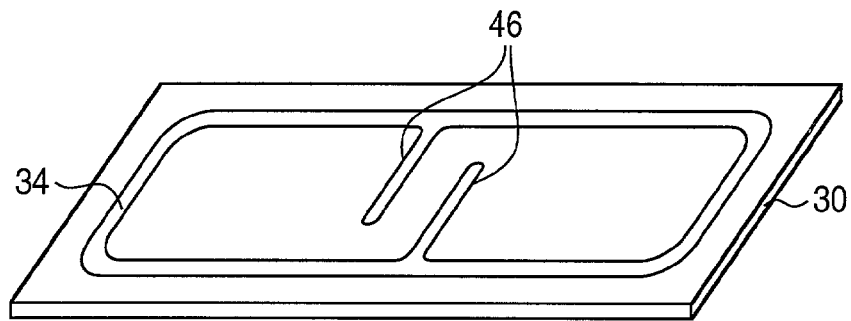
FIG. 2B illustrates form-in-place gasket including structural features disposed on a substrate surface.
Figure 2C:
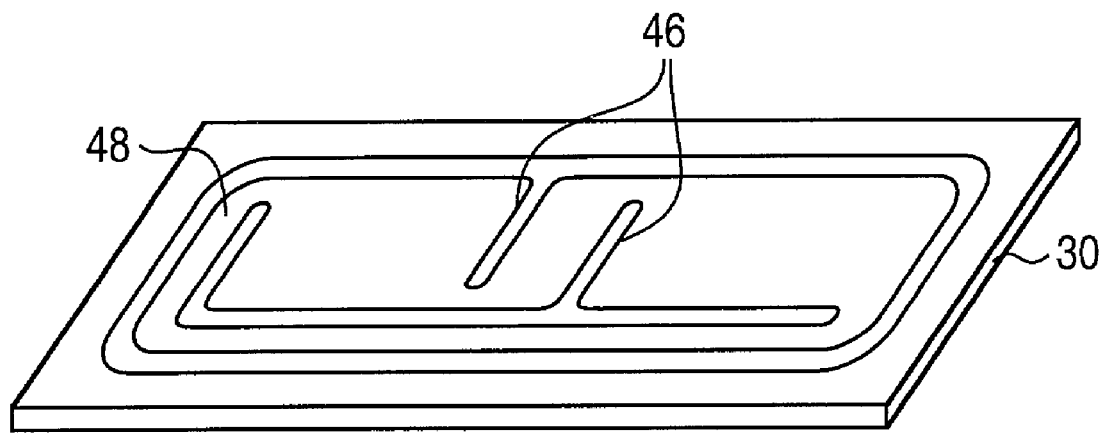
FIG. 2C shows a form-in-place gasket forming a vent.
Figure 2D:
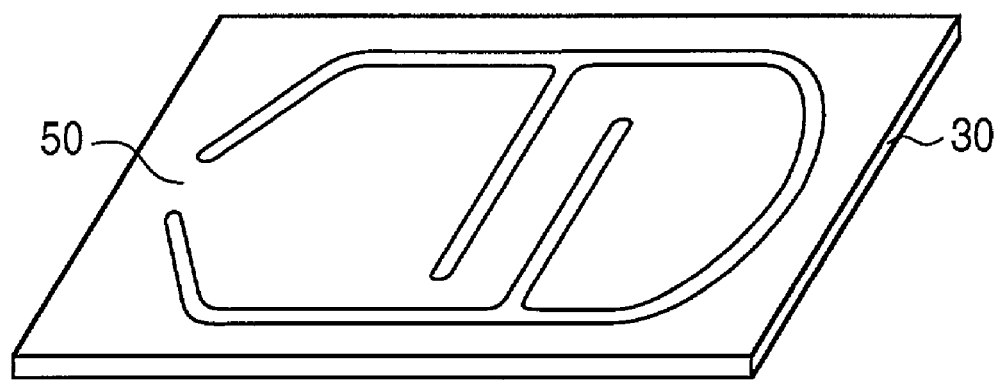
FIG. 2D shows structural features including a vent, or port.

FIGS. 2B, 2C, and 2D provide a few examples of how the form-in-place gasket 34 may have a variety of structural features. FIG. 2B illustrates a form-in-place gasket 34 on a substrate 30 where the form-in-place gasket 34 has internal structural features 46. These structural features 46 may serve functions such as enhancing mixing of fluids, partitioning fluids in separate reservoir chambers until needed for mixing or rinsing, or other desired functions that may be apparent to the skilled practitioner given the disclosure herein. FIG. 2C illustrates a form-in-place gasket 34 with more internal structural features 46, this time including an internal vent 48 that provides for enhanced fluid flow during use of the illustrated device. FIG. 2D illustrates a form-in-place gasket 34 with a different structural feature 50 that may function as an external vent or as a port to supply or remove fluid from the chamber. Some embodiments may provide for ports through the substrate 30 or through the cover 40 to supply or remove fluid from the chamber. In each of the embodiments illustrated in FIGS. 2B-2D, a cover 40 may be disposed adjacent the substrate 30 with the gasket between the substrate and cover to form an assay chamber.

The gasket material may deposited on the substrate in predetermined configurations which include structural features, such as, for example, gaps, protrusions, vents, channels, mazes, serpentine channels, bumps, sample inlets, and/or sample outlets. These structural features can be used to enhance performance of the system, such as by directing fluid flow, partitioning fluids, or enhancing mixing of fluids. Additional devices, such as chemically derivatized beads and filters, can be glued in place and sealed as part of the gasket structure. Interior areas on the substrate surface defined by form-in-place gasket may also serve as wells for retaining fluid (fluid containment structures). Multiple areas may be defined on a single substrate (see FIG. 4), allowing different samples to be applied to and analyzed on a single substrate, thus potentially reducing cost, increasing throughput, or increasing the number of different analytes which can be tested on a single substrate. It can be seen from the figures that the gasket material may be deposited on the substrate to form continuous structures (those that may be deposited without halting and restarting the application of the gasket material), like shown in FIG. 2A, or discontinuous structures (those that require halting the application of the gasket material and restarting application at a different point on the substrate surface), like those shown in the other figures. In some embodiments, other fluid handling features such as, for example, gaps, protrusions, vents, channels, mazes, serpentine channels, bumps, ports, sample inlets, and/or sample outlets may be present on the substrate or otherwise associated with the assay chamber.

The gasket material is selected to provide a form-in-place gasket having suitable thickness and flexibility to enable a fluid tight seal where needed for the desired configuration. In one embodiment, the gasket material is cured on the substrate in the absence of a cover, with a cover optionally being placed on the gasket after curing of the gasket material. An alternate embodiment provides that the cover is put in place before curing of the gasket material, thus providing a form-in-place gasket where the gasket is formed between the substrate and the cover. In one embodiment, the gasket material is selected so that, when it is cured prior to positioning the cover over the assay site, the cover may be removed from contact with the gasket without significant damage to the form-in-place gasket, allowing the cover (or a different cover) to be re-positioned over the assay site to form a seal (i.e. the gasket is re-usable). In an alternate embodiment, the cover is put in place prior to the curing of the gasket material, and then the gasket material is allowed to cure with the cover in place. This type of seal typically leads to damage of the gasket upon removal of the cover; in this case the seal may be formed only once (i.e. gasket may not be re-used, or the seal may not be re-formed after breaking, or the seal not intended to be broke in normal use of the device). This type of seal may be termed a "non-releasable" seal, or a "permanent seal", meaning that the seal is not adapted to being broken and then reformed.

Any material having suitable characteristics may be used as a gasket material. Gasket materials are generally fluid materials that can be cured to provide a gasket having suitable characteristics. Selection of a gasket material is determined relative to the intended application. Suitable gasket materials include, e.g. silicone sealants, urethanes, and polysulfides. Still other suitable gasket materials are, e.g. latex, and acrylic sealants. In all types of gaskets cured on a substrate in the absence of a cover, a low durometer material is used to allow for a compression seal. Silicone sealant materials are available in many formulations that are suitable for use in the process of making form-in-place gaskets according to the current invention. For very thin gaskets, with dimensions from about 20 to about 100 micrometers thick, a self-leveling, low viscosity, fluid material should be selected. Thicker gaskets can use a wider range of materials including higher viscosity material to non-slumping or paste materials. For the relatively thin gaskets, a suitable formulation should provide for a silicone gasket that remains highly flexible and durable after curing. By using a low viscosity (about 15,000 to about 50,000 cps, or centipoises) silicone that is "self leveling", a very small bead of silicone can be applied to a gasket surface. Being self-leveling, the small bead of silicone will spread out to a thin profile, or cross section. In some embodiments, the silicone will have a viscosity in the range of about 20,000 to about 40,000 cps, or even in the range of about 25,000 to about 35,000 cps. In other embodiments, the viscosity may be in the range of about 50,000 to about 80,000 cps. Other embodiments may use a gasket material that is non-slumping. In certain embodiments of the invention, the preferred gasket material is a silicone sealant material such as RTV 118 available from FE Silicones (Charlotte, N.C.), RTV 734 or 3-1753 (both available from Dow Corning (Midland, Mich.)). An example of a paste silicone adhesive that is a thermal cure silicone is GE 6124. Gasket materials may also be selected based on their hardening properties—a gasket material that forms a soft, rounded profile gasket that is compressible may be desirable for forming fluid-tight seals where tolerances between substrate and cover may vary; however, a less soft, less compressible gasket may be desired for other applications.

The gasket material may be applied to the gasket surface by any suitable method, e.g. silk screen, brush, spray, or transfer process. For example, to apply a pattern of the gasket material using a pad transfer process, a negative relief of the pattern is generated so that the desired thickness of the adhesive is the depth of the relief in the mold. The mold is then covered with the gasket material and pressed into the mold, and the excess is scraped off. A flexible pad is then pressed onto the relief area and the gasket material is transferred from the mold to the surface of the pad. The pad is then moved into the desired position for the gasket. As the pad contacts the surface (e.g. the substrate surface), again the gasket material is transferred from the pad onto the surface. A company that manufactures and distributes pad printing technologies is Printex, A Division Of Pemco Industries, Inc. (Poway, Calif.).

In one embodiment, the method of applying the gasket material to the gasket surface uses a dispensing system designed for adhesive sealants. The dispensing system has an x-y-z positioning system and is programmable to allow the application of a thin bead of silicone onto the gasket surface in the desired configuration. A suitable system is the Automove 403 and is available from Asymtek (Carlsbad, Calif.). The use of such a dispensing system is described below in the examples.

The gasket surface in certain embodiments should be relatively smooth. In an alternate embodiment, the gasket surface is etched, chemically treated, or scarified to provide greater adhesion of the gasket material. After the gasket material is deposited in the predetermined configuration at the desired site, the gasket material is allowed to cure to form the form-in-place gasket. Various methods of curing depend on the properties of the materials. One part adhesives have the advantage of only needing to dispense, transfer, paint or spray one material and do not require any mixing of two or more materials prior to use or after in place. One part adhesives are cured depending properties of the material. For one part adhesives, curing can be done by moisture cure, such as moisture cure RTV silicone where moisture in the air reacts with the silicone. Typical cure times for these RTV silicones are from 1 to several days. In some embodiments the gasket material may be exposed to heat to cause or to speed up the curing process. Heat cure gasket material, such as heat cure silicone, are cured by a process of heating the material well above room temperature for a described time, typically 1 to 2 hours. There are also UV cure adhesives where the material is exposed to UV light. This are typically fast curing times in as little as 1 minute. Multiple part adhesives are also available where a curing agent is mixed into the material before application, mixed during the dispensing, or sprayed on before or after application. The curing agent is typically a catalyst to the curing process. The disadvantage of multipart adhesives is that one has to handle more than one material and if premixed, a working time is associated with the material. A cover having a mating surface that is complementary to the gasket surface can be placed over the substrate, forming a fluid tight seal between the substrate and the cover.

Figure 3:
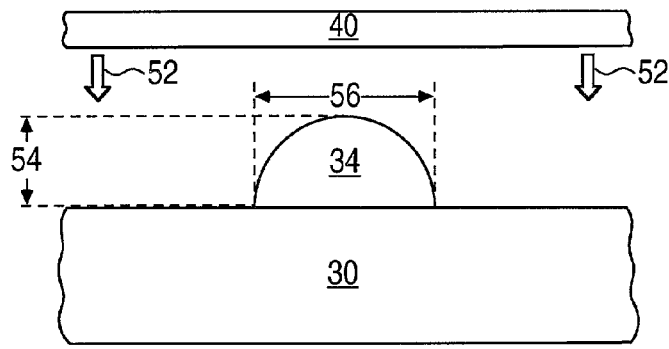
FIG. 3 is a cross-sectional view showing the profile of a bead of gasket material on a substrate.

The physical dimensions of the form-in-place gasket may be characterized in terms of thickness, width, and length. Thickness is defined as the perpendicular distance from the gasket surface to most distal surface of the applied gasket, when the cover is not in place. When the cover is in place, the thickness is the perpendicular distance between the gasket surface and the mating surface of the cover at the location of the form-in-place gasket. 'Thin' refers to the thickness of an item, such as a gasket, and a 'thin cross section' references a cross section that is of limited thickness. The width of the gasket is defined as the distance from one side of the gasket material through the gasket material to the opposing side of the gasket material, proceeding on a line parallel to the gasket surface but perpendicular to gasket's long axis at the particular point where the length is being measured. 'Narrow' refers to the width of an item, and a 'narrow cross section' references a cross section that is of limited width. The length is the distance traced around the perimeter of the area, space, or chamber enclosed by the gasket. The length is typically much larger than the thickness or width. The gasket's long axis at any point is defined by the direction in which length is measured at that point. The cross section of the gasket refers to the area (or shape) of that portion of a plane through which the gasket passes, the plane being perpendicular to the long axis of the gasket (the axis along which length is determined). FIG. 3 schematically illustrates a cross section of a form-in-place gasket 34 formed on a substrate 30 with a cover ready to be put into place on the form-in-place gasket 34 (move in the direction of the arrows 52). FIG. 3 also schematically illustrates the meaning of thickness (denoted by arrows 54) and width (denoted by arrows 56). The length of a form-in-place gasket is dictated by the structure of the substrate, the cover, and of the area, space, or chamber defined by the gasket, substrate, and cover. The thickness of a gasket is generally dictated by the choice of gasket material and method and/or conditions of application of the gasket material (including amount of pressure applied, if any, to squeeze the substrate and cover together). The width of the gasket material may also be dictated by the choice of gasket material and the method and/or conditions of application of the gasket material (including whether the cover is applied before curing of the gasket material). The thickness and width of the gasket may be widely varied and may be selected based on the desired characteristics of the device being made.

Using the methods described herein, the thickness of the gaskets are typically at least about 10 micrometers, more typically at least about 15 micrometers, preferably at least about 20 micrometers, and the thickness may range up to about 25 micrometers in some embodiments, up to about 50 micrometers in other embodiments, and up to about 100 micrometers, or even about 250 micrometers in still other embodiments. In larger scale devices (such as where assay chambers larger than about 2 milliliters are contemplated) the thickness may be up to about 250 micrometers in certain embodiments, up to about 500 micrometers in some embodiments, up to about 1000 micrometers or even up to about 2500 micrometers in yet other embodiments. Using the methods described herein, the width of the gasket is at least about 100 micrometers, typically at least about 150 micrometers, more typically at least about 200 micrometers, at least about 250 micrometers in some embodiments, more preferably at least about 300 micrometers in certain embodiments, and the width may range up to about 250 micrometers in other embodiments, or up to about 400 micrometers, or even up to about 500 micrometers in other embodiments, or up to about 700 micrometers, or even up to about 1000 micrometers in particular embodiments. In larger scale devices (such as where assay chambers larger than about 2 milliliters are contemplated) the width may range up to about 1.5 millimeters, typically up to about 3 millimeters, more typically up to about 6 millimeters.

The thickness and/or width may be influenced by the characteristics of the gasket material (e.g. viscosity) and the conditions under which it is applied and/or cured, including whether a cover is in place (pressed with the mating surface against the gasket material) during curing and how much pressure is applied to the cover. The choice of gasket material will thus influence the physical dimensions of the gasket, and the desired physical dimensions of the gasket will influence the choice of gasket material. A range of gasket thickness may be obtained by varying the process suitably, for example by varying the choice of gasket material or the method used to apply the gasket material to the substrate.

Other embodiments may use a gasket material, e.g. either a self-leveling or a non-slumping gasket material, to form a fluid containment structure, e.g. a well, on a substrate by depositing the gasket material onto a substrate in a configuration in which the gasket material is at the perimeter of an interior area of the substrate (defining the interior area), the gasket material and interior area providing a well that may be used as to confine a fluid to the interior area. In a particular embodiment, an analysis component is in operable relation to the fluid containment well, such that in use, while the fluid containment well operates to confine the sample fluid, the analysis component is used in the analysis of the sample fluid. In one embodiment, the present invention provides a method for making a form-in-place gasket on a gasket surface on a substrate so that the form-in-place gasket is adjacent to a biochemical assay site. In this embodiment, the method comprises making the form-in-place gasket having a desired configuration by depositing a suitable gasket material in a predetermined configuration onto the gasket surface at a site adjacent a biochemical assay site, and then curing the gasket material to provide the finished form-in-place gasket having the desired configuration. The gasket material is selected to provide a finished gasket that is flexible, inert to the conditions under which the biochemical assay is conducted, and having a very thin cross section. In this regard, "biochemical assay site" references an analysis site at which a biochemical assay is intended to occur. A biochemical assay is an assay that is intended to analyze an analyte containing a biomolecule or which uses a biomolecule to analyze an analyte, such as a hybridization assay using a bioarray to analyze a sample fluid. The biochemical assay site generally includes at least one analysis component, e.g. a biochemical reagent, or is adapted to receive at least one analysis component. The biochemical assay site may optionally include a sensor for enabling sensing of results of the biochemical assay. In one embodiment, the method comprises making the form-in-place gasket having a desired configuration by depositing a suitable gasket material in a predetermined configuration onto the gasket surface at a site which, upon further assembly, will be adjacent a biochemical assay site, and then curing the gasket material to provide the finished form-in-place gasket having the desired configuration.

The invention provides for an assay chamber associated with or including a biochemical assay site. The assay chamber includes a substrate that has a gasket surface with a form-in-place gasket on the gasket surface. The assay chamber also includes a cover having a mating surface that is complementary to the gasket surface and that can be placed adjacent the substrate to form a fluid-tight assay chamber. To form an assay chamber, the gasket surface should be adapted to fit the mating surface of the cover. In certain embodiments the assay chamber further includes at least one analysis component (e.g. an array of immobilized oligonucleotides) necessary for performing a biochemical assay, such as, e.g. a binding reaction between an immobilized oligonucleotide and a complementary oligonucleotide in the sample solution. In one embodiment, the biochemical assay chamber is formed by a process where the gasket material is first cured to form the form-in-place gasket, and then a cover is placed adjacent the substrate with the form-in-place gasket disposed between the cover and the substrate. In another embodiment, the cover is first placed on the gasket material, and then the gasket material is cured. The assay chamber may have an alternate configuration that provides for the biochemical assay; for example, the gasket surface may be on the cover, with the form-in-place gasket formed on the cover rather than on the substrate—in such case the complementary surface is on the substrate. Assay chambers according to the current invention may hold any volume of fluid that the assay chambers may be designed to hold. In some embodiments the volume of the assay chamber may be at least about 0.1 microliter, or at least about 1 microliter, or at least about 10 microliters, or at least about 100 microliters, depending on the desired design of the assay chamber. In some embodiments the volume of the assay chamber may up to about 100 microliters, or up to about 1 milliliter, or up to about 10 milliliters. In designs for handling larger amounts of fluid, the volume of the assay chamber may be up to about at 10 liters or more, depending on the desired design of the assay chamber.

It is commonly known that some analytes cause absorption of light of certain wavelengths, and some analytes produce changes in fluorescence of a detector molecule. Thus, it is contemplated that both light absorption and fluorescence can be used for sensing the presence and concentration of certain analytes. As used herein, the term "light interaction" refers to light absorption, fluorescence, phosphorescence, luminescence, and the like, occurring at an analysis site. In some embodiments, analysis of an analyte in the assay chamber uses a light detector associated with the assay chamber to measure the light interaction. It is to be understood that other types of light interaction may be monitored (as with a detector) to determine the presence and concentration of analytes in view of the present disclosure.

In embodiments including arrays in the assay chambers, well know art provides teaching for manufacture and use of the arrays, and it is within ordinary skill to use and to adapt this art to provide arrays on substrates such as are used herein in connection with the invention. Such art includes U.S. Pat. No. 6,242,266 to Fisher, U.S. Pat. No. 6,232,072 to Schleifer et al., U.S. Pat. No. 6,180,351 to Cattell, U.S. Pat. No. 6,171,797 to Perbost, U.S. Pat. No. 6,323,043 to Caren et al., U.S. Pat. No. 5,599,695 to Pease et al., U.S. Pat. No. 5,753,788 to Fodor et al., U.S. Pat. No. 6,329,143 to Stryer et al., U.S. Pat. No. 6,371,370 to Sadler et al., U.S. Pat. No. 5,721,435 to Troll, U.S. Pat. No. 5,763,870 to Sadler et al., and U.S. Pat. No. 6,403,957 to Fodor et al. In certain embodiments, the analysis site may be adapted for use with commercially available optical scanning systems, examples of which are described in U.S. Pat. No. 5,837,475, U.S. Pat. No. 5,760,951 (confocal scanner) and U.S. Pat. No. 5,585,639 (off axis scanner), all incorporated herein by reference. Typical scanning fluorometers are commercially available from different sources, such as Molecular Dynamics of Sunnyvale, Calif., General Scanning of Watertown, Mass., Hewlett Packard of Palo Alto, Calif. and Hitachi USA of So. San Francisco, Calif. Analysis of the data, (i.e., collection, reconstruction of image, comparison and interpretation of data) is performed with associated computer systems and commercially available software, such as IMAGEQUANT™ by Molecular Dynamics or GENE-CHIP™ by Affymetrix of Santa Clara, Calif. Typically, a laser beam or other light source is used to illuminate the analysis site, which excites fluorescent labels used in the assay. The fluorescence signal is detected by a detector and processed by a computer to determine information about the analyte, such as concentration, identity, and/or binding affinity.

In varying embodiments, different arrangements wherein the array is interrogated without removing the array from the chamber may easily be envisioned, for example the cover is made of transparent glass or plastic and the array reader is adapted to interrogating the array through the transparent glass or plastic cover. In such an embodiment the chamber may include an inlet port and an outlet port, to allow introduction and removal of, e.g., target solution (the analyte), rinsing solution, or other reagents.

Figure 4:
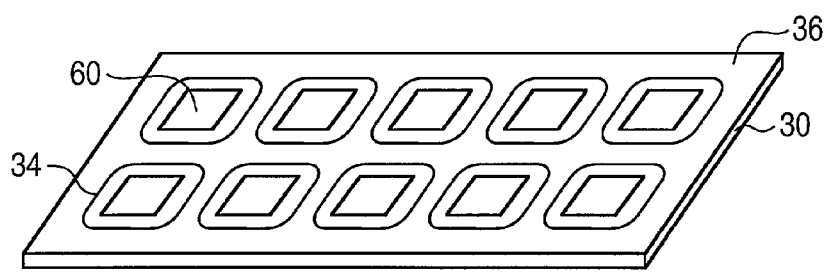
FIG. 4 shows a multiple array substrate with gaskets around individual arrays.

FIG. 4 depicts an embodiment with multiple fluid containment structures and multiple biochemical assay sites. In certain embodiments the biochemical assay sites comprise an array 60, for example a bioarray, that is to be used in a biochemical assay. It should be understood that the biochemical assay (such as, in an embodiment, a bioarray) may be manufactured directly onto the substrate surface 36 or may be manufactured on an alternate material that is then immobilized on the substrate, for example in a well or a depression in the substrate surface. The invention will be herein described as it relates to arrays 60 on the substrate 30, but it should be apparent that any suitable biochemical assay may be substituted in place of the array 60 by one of skill in the art given the disclosure herein. A skilled practitioner will be able to adapt methods of manufacturing bioarrays that are known in the art to provide one or more bioarrays on the substrate. Such known methods are described in U.S. patents and other references cited herein.

Referring now to FIG. 4, the invention as described herein may be practiced in an embodiment wherein one or more arrays 60 (e.g. bioarrays) are disposed on the substrate surface 36 of a single substrate 30. The substrate surface 36 further has a plurality of form-in-place gaskets 34 disposed thereon, each form-in-place gasket 34 encircling one or more arrays 60. One or more covers (not shown) may be disposed closely adjacent the substrate and contacting the form-in-place gaskets 34 to form a fluid tight seal around each array 60. In some embodiments, ports (e.g. inlet and/or outlet) may be present, for example in the cover, allowing fluidic assess to the assay chamber defined by the substrate surface, the cover, and the form-in-place gasket. In the embodiment depicted in FIG. 4, the arrays 60 produced on a given substrate 30 need not be identical and some or all could be different from the other arrays 60 present on the given substrate 30.

In one embodiment, about 2 to 100 of such bioarrays can be fabricated on a single substrate (such as glass). In such embodiment, after the substrate has the biomolecules on its surface, the substrate may be cut into substrate segments, each of which may carry one or two or more bioarrays. In such cases gasket material may be deposited in predetermined configurations onto the substrate before and/or after the substrate is cut into substrate segments. The narrow gaskets that form around the individual areas of a multiple array substrate would be easier to form a seal that a traditional single gasket with multiple openings. Where a pattern of bioarrays is desired, any of a variety of geometries may be constructed, including for example, organized rows and columns of bioarrays (for example, a grid of bioarrays, across the substrate surface), a series of curvilinear rows across the substrate surface (for example, a series of concentric circles or semi-circles of bioarrays), and the like. One or more analysis components may be associated with each bioarray. The gasket material may, in one embodiment, make a closed loop around each bioarray as shown in FIG. 4. In other embodiments, the predetermined configuration for applying the gasket material may leave one or more gaps (ports, or inlets and outlets) as in FIG. 5.

Figure 5:
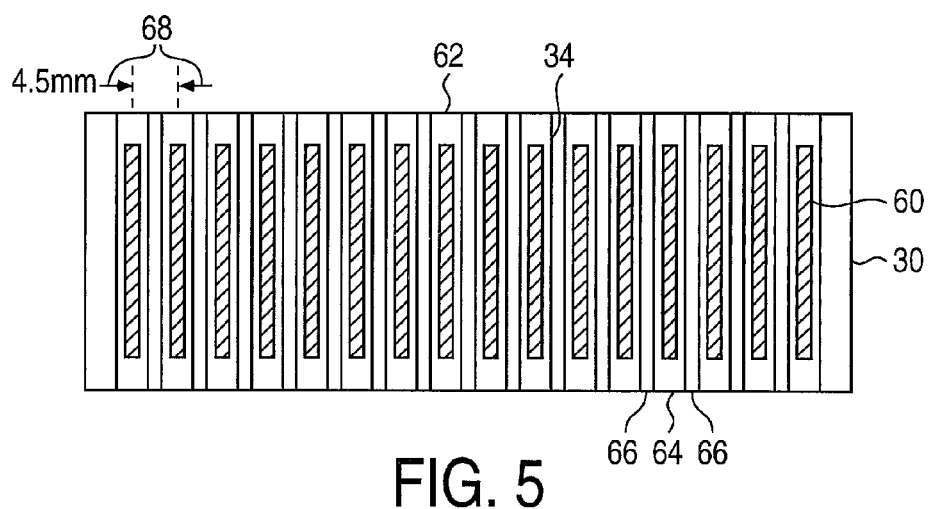
FIG. 5 is a drawing of a multiple array substrate formatted to interface with parallel fluid handling equipment.

In some embodiments the invention provides multiple arrays on a single substrate, wherein multiple assay chambers are formed as described herein by one or more covers disposed over the single substrate, wherein a form-in-place gasket is disposed between the cover(s) and substrate. An exemplary embodiment is illustrated in FIG. 5 showing a multiple array substrate with form-in-place gaskets 34. A substrate 30 with a substrate surface 36 has a plurality of individual arrays 60 disposed thereon. The substrate 30 also has form-in-place gaskets 34 disposed alongside the individual arrays 60 extending from an inlet site 62 to an outlet site 64, as shown in FIG. 5. In some embodiments the form-in-place gasket may be formed onto one or more covers adapted to being disposed on the substrate. In certain embodiments both the substrate and the cover will have form-in-place gaskets. When a cover (not shown) is placed in position on the substrate 30, a series of parallel assay chambers is formed, each assay chamber defined by the substrate, the cover, and the form-in-place gaskets. Each assay chamber will include one or more arrays, depending on the design. Each assay chamber has an inlet defined by the cover, form-in-place gasket 34, and substrate 30 at inlet site 62. Similarly, each assay chamber has an outlet defined by the cover, form-in-place gasket 34, and substrate 30 at outlet site 64. Fluid may be introduced into the assay chamber via the inlet, and the outlet serves to vent the assay chamber and/or provide a way for the fluid to leave the assay chamber. It will be appreciated that further liquid handling structures may be included, using the deposited gasket material or other well known manufacturing techniques to include e.g. fluid reservoirs, flow conduits, vents, mixing structures, and the like. It will also be appreciated that similar arrangements of elements are within the intended scope of the invention, e.g. a substrate supporting multiple arrays disposed thereon may be mated against a cover having a form-in-place gasket to form multiple assay chambers.

The embodiment shown has arrays 60, inlets, and outlets equidistantly disposed across the substrate, that is, they are spaced at uniform intervals. Assay chambers are provided by a cover disposed adjacent the substrate with the form-in-place gasket between the substrate and the cover, and the assay chambers are spaced at uniform intervals. As indicated in FIG. 5 (at the arrows 68), the arrays are disposed on 4.5 mm centers, which is compatible with the form factor of microassay plates that have a 16×24 array of wells (e.g. 384 well microtiter plates) and also compatible with fluid handling equipment (e.g. an automated fluid dispensing system) designed to be used with such microassay plates. The multiple array substrate may be fabricated in other configurations, for example, with the arrays disposed on 9 mm or 2.25 mm centers on the substrate, in which case the multiple array substrate would be compatible with the form factor of microassay plates that have a 8×12 array of wells (e.g. 96 well microtiter plates) or a 32×48 array of wells (e.g. 1536 well microtiter plates), respectively, and also compatible with fluid handling equipment (e.g. automated fluid handling equipment) designed to be used with such microassay plates. In some embodiments, the multiple array substrates may include more arrays on a substrate, e.g. from about 8 or 12 arrays per substrate or even from about 16 or 24 arrays per substrate or even from about 32 or 48 arrays per substrate, up to about 96 arrays per substrate, or even up to about 384 arrays per substrate, or even up to about 1536 arrays per substrate, or even more. In some embodiments, the substrates may be stacked such that the backside of a first substrate may serve as the cover for a second substrate, with a form in place gasket formed on either the backside of the first substrate or the surface of the second substrate. Stacking multiple substrates in such a fashion would provide a multiple array unit having many individual assay chambers, each with one or more arrays. A similar unit would be formed by alternately stacking multiple array substrates with covers. The multiple array substrates described thus may be used to perform multiple array hybridization assays in a large scale parallel format, greatly increasing throughput as compared to individual (or small multiple, i.e. less than about 3 arrays per substrate) array substrates.

Figure 6:
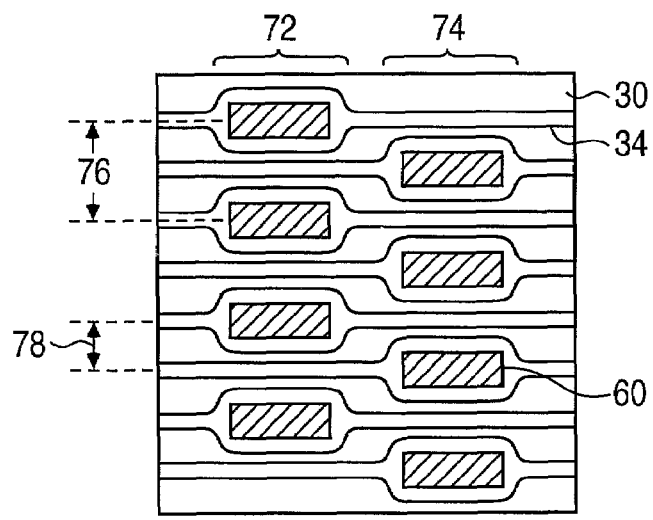
FIG. 6 is a drawing of a multiple array substrate formatted to interface with parallel fluid handling equipment, wherein the multiple array substrate provides for assay chambers arranged in a plurality of ranks.
Figure 7:
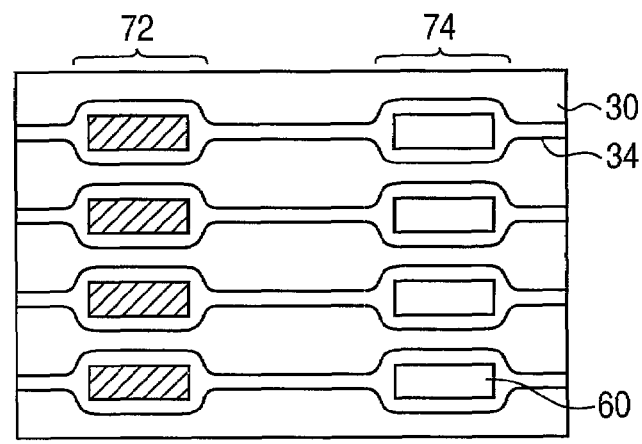
FIG. 7 is a drawing of a multiple array substrate formatted to interface with parallel fluid handling equipment, wherein the multiple array substrate provides for assay chambers arranged in a plurality of ranks.

Still other embodiments are illustrated in FIGS. 6 and 7. In FIG. 6, form-in-place gaskets 34 are disposed on a substrate 30 in a configuration providing for a plurality of assay chambers arranged in ranks 72, 74, wherein the assay chambers in a given rank are equidistantly disposed (spaced at uniform intervals). Note that the arrays 60 on the substrate 30 are equidistantly disposed at a different uniform interval (arrows 76) than the uniform interval (arrows 78) of the inlets and outlets, due to the arrangement into ranks 72, 74. In FIG. 7, the form-in-place gaskets 34 are disposed on a substrate 30 in a configuration providing for a plurality of assay chambers arranged in ranks 72, 74, wherein the assay chambers are arranged "in series" between the ranks such that an assay chamber in the first rank is in fluid communication with an assay chamber in the second rank. In an embodiment having assay chambers in series, the sample fluid may be pumped into the first assay chamber, then more fluid may be introduced, pushing the sample fluid into the second assay chamber, then the fluid may be withdrawn from the first chamber (reverse flow) such that the sample fluid is transferred from the second chamber back into the first chamber. This may be repeated several times to provide mixing of the sample fluid and improved contact between the sample and any analysis component (e.g. an array) associated with the first assay chamber.

To form the array, the biomolecule is typically applied to a surface, e.g. the surface of the substrate, by spotting, using pipettes, pins, inkjets, or the like. Methods of depositing materials onto a planar surface are known, including loading and then touching or tapping a pin or capillary to the surface (U.S. Pat. No. 5,807,522 to Brown et al.; U.S. Pat. No. 6,110,426 to Shalon, et al.); employing an array of pins or capillaries to transfer an array of droplets to a surface (Lehrach, et al., "Hybridizidation Fingerprinting in Genome Mapping and Sequencing," in Genome Analysis, Vol. 1, pp. 39-81 (1990, Davies and Tilgham, Eds., Cold Spring Harbor Press)). Ink jet technology may be used to spot biomolecules and other reagents on a surface, for example, using a pulse jet such as an inkjet type head to deposit a droplet of reagent solution for each feature. See, for example, PCT publications WO 89/10977, WO 95/25116 and WO 98/41531, and elsewhere. Still other methods and apparatus for fabrication of polynucleotide arrays are described in, e.g. U.S. Pat. No. 6,242,266 to Schleiffer et al., which describes a fluid dispensing head for dispensing droplets onto a surface, and methods of positioning the head in relation to the surface. Other methods include those disclosed by U.S. Pat. No. 6,180,351 to Cattell; U.S. Pat. No. 6,171,797 to Perbost; Gamble, et al., WO97/44136; Gamble, et al., WO98/10858; Baldeschwieler, et al., WO95/25116; and the like. Other methods can also be used to deposit biomolecules on the surface including those employing photolithographic techniques for forming arrays of moieties, such as described in U.S. Pat. Nos. 5,807,522; 5,143,854; 5,405,783; and 5,744,305. A number of other known methods are available and may be used for depositing the biomolecules on a surface.

Modifications of these known methods within the capabilities of a skilled practitioner in the art as well as other methods known to those of skill in the art may be employed.

In one embodiment, the bioarray has array features comprising oligopeptides deposited on the surface of the substrate. In other embodiments, other biomolecules, such as polypeptides, oligonucleotides, polynucleotides, or known analogues or derivatives of any of the foregoing, or combinations of any of the foregoing, are deposited on the substrate. Any given array feature can have the same or a different biomolecule or combination of biomolecules compared to any other given array feature. Biomolecules may be derived from natural sources (e.g. isolated from cellular material) or may be synthetic. Examples of biomolecules include antigenic epitopes, fragments of antibodies or other proteins, polysacharrides, cDNAs, and RNAs.

The biomolecules may bind directly to the substrate surface or may bind via an intermediate moiety upon the surface, e.g. a bifunctional linker molecule or other surface treatment. Polynucleotides may be bound to the surface by irradiating with UV light, during which the polynucleotides covalently attach to the surface, typically via an intermediate moiety, presumably, by non-specific, free-radical cross-linking. Chemical methods for covalently binding biomolecules in an array format to substrate surfaces are known in the art and may be employed by one of ordinary skill in the art.

In bioarray fabrication, the quantities of biomolecule available are usually very small and expensive. Additionally, sample quantities available for testing are usually also very small and it is therefore desirable to simultaneously test the same sample against a large number of different probes on a bioarray. Therefore, one embodiment of the invention provides for fabrication of bioarrays with large numbers of very small, closely spaced array features. Arrays may be fabricated with array features that may have diameters (assuming a round spot) in the range from a minimum of about 10 micrometers to a maximum of about 1.0 cm. In embodiments where very small spot sizes or array feature sizes are desired, material can be deposited in small spots whose width is in the range about 1.0 micrometer to 1.0 mm, usually about 5.0 micrometers to 0.5 mm, and more usually about 10 micrometers to 200 micrometers. Interfeature areas will typically (but not essentially) be present which do not carry any biomolecule. It will be appreciated though, that the interfeature areas could be of various sizes and shapes.

A bioarray may contain any number of array features, generally including at least tens of array features, usually at least hundreds, more usually thousands, and as many as a hundred thousand or more array features. All of the array features may be different, or some or all could be the same. Each array feature carries a predetermined biomolecule or a predetermined mixture of biomolecules, such as a particular polynucleotide sequence or a predetermined mixture of polynucleotides. The array features may be arranged in any desired pattern, e.g. organized rows and columns of array features (for example, a grid of features across the substrate surface), a series of curvilinear rows across the substrate surface (for example, a series of concentric circles or semi-circles of features), and the like. In embodiments where very small array feature sizes are desired, the density of features on the substrate may range from at least about ten array features per square centimeter, or preferably at least about 35 array features per square centimeter, or more preferably at least about 100 array features per square centimeter, and up to about 1000 array features per square centimeter, or preferably up to about 10,000 array features per square centimeter, or perhaps up to 100,000 array features per square centimeter.

The substrate and the cover may take any of a variety of conformations ranging from simple to complex. Thus, the substrate could have generally planar form, as for example a slide or a plate, such as a rectangular- or square- or disc-shape. In many embodiments, the substrate will be shaped generally as a rectangular solid, having a length in the range about 4 mm to 400 mm, usually about 4 mm to 150 mm, more usually about 4 mm to 125 mm; a width in the range about 4 mm to 400 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. In other embodiments the substrate may have larger dimensions. The substrate surface may be smooth or substantially planar, or have irregularities, such as depressions or elevations. The shape of the substrate may be selected according to manufacturing, handling, and use considerations. The cover will be shaped to provide a mating surface that is complementary to the gasket surface of the substrate such that the cover can be positioned against the form-in-place gasket to form a fluid tight seal. The cover may be smooth or substantially planar, or have irregularities, such as depressions or elevations.

The process of the current invention may be employed on any substrate having a surface to which the gasket material may bind. Preferred substrate materials provide physical support for the gasket material and endure the conditions of the deposition process and of any subsequent treatment or handling or processing that may be encountered in the use of the substrate. Suitable substrates may have a variety of forms and compositions and may derive from naturally occurring materials, naturally occurring materials that have been synthetically modified, or synthetic materials. Examples of suitable substrate materials include, but are not limited to, nitrocellulose, glasses, silicas, teflons, metals (for example, gold, platinum, and the like), and ceramics (including aluminum oxide and the like), composites, and laminates thereof. Suitable substrate materials also include polymeric materials, including polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, polyesters, including poly(ethylene terephthalate) and poly(butylene terephthalate); polyamides, (such as nylons); polyethers, including polyformaldehyde and poly(phenylene sulfide); polyimides, such as that manufactured under the trademarks KAPTON (DuPont, Wilmington, Del.) and UPILEX (Ube Industries, Ltd., Japan); polyolefin compounds, including ABS polymers, Kel-F copolymers, poly(methyl methacrylate), poly(styrene-butadiene) copolymers, poly(tetrafluoroethylene), poly(ethylenevinyl acetate) copolymers, poly(N-vinylcarbazole), polytetrafluoroethylene, polypropylene, polystyrene, polycarbonate, and blends thereof, and the like. Certain polymeric materials that may be used for substrate materials include organic polymers that are either homopolymers or copolymers, naturally occurring or synthetic, crosslinked or uncrosslinked. The cover may be formed from the same types of materials as given herein for the substrate.

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite.

The substrate surface may optionally exhibit surface modifications over a portion or over all of the surface with one or more different layers of compounds that serve to modify the properties of the surface in a desirable manner. Such modifications include: inorganic and organic layers such as metals, metal oxides, conformal silica or glass coatings, polymers, small organic molecules, hetero-bifunctional linking molecules, and the like. Polymeric layers of interest include layers of: polypeptides, proteins, polynucleotides or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto, e.g. conjugated.

Components of the assay chambers (e.g. covers, substrates, etc.) according to the present invention can be fabricated using any convenient method, including, but not limited to, molding and casting techniques, embossing methods, surface machining techniques, bulk machining techniques, and stamping methods. Further, injection molding techniques well known in the art may be useful in shaping the materials used to produce components according to the instant invention.

Typical use of the system is given in the examples which follow, which illustrate various embodiments according to the present invention but should not be construed to limit the invention as claimed.

EXAMPLES

The practice of the present invention will employ, unless otherwise indicated, conventional techniques of device manufacture, material molding and shaping, applying coatings, synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Forming the Form-in-place Gasket

An example of a process of making a form-in-place gasket using a controlled dispensing system, in this example an adhesive dispensing machine, is now described. The dispensing system has a computer controlled positioning system to control the position and feed rate of a dispensing tip. The computer may be programmed to control delivery of gasket material from the dispensing tip. A suitable system is the Automove 403 and is available from Asymtek (Carlsbad, Calif.). The type of gasket, whether thin or thick, and the shape or profile, will determine the types of gasket material appropriate for the application. For thin gaskets, one would select a low viscosity, self-leveling material. One would select a small diameter orifice dispense tip, in the 25 to 29 gauge range; a small diameter dispense tip keeps the amount of material dispensed and the diameter of the bead small. When using small diameter tips, the dispense rate is also low requiring a slow velocity of the dispense tip. Experimenting has shown that dispense tip velocities of more than about 0.01 inches per second and less than about 10 inches per second are suitable for the thin gaskets, though the dispense tip velocity may extend higher or lower in certain embodiments. For the thin gaskets, it is desirable to tightly control the parallel travel of the dispense tip with respect to the substrate surface where the gasket will be placed as well as the height of the dispense tip above the surface. Since the typical distance of the tip above the surface is between 0.002 and 0.005 inches, changes in the height due to unparallel travel of the tip is significant. For thicker gaskets, adjustments would be made, including one or more of, e.g. a larger diameter dispense tip, a non-slumping gasket material, altering the angle and height of the dispense tip relative to the gasket surface, etc. The amount of gasket material dispensed and the rate at which the gasket material is dispensed affect the uniformity of the gasket height (thickness). The simplest dispense system is the pressure regulated syringe. The feed rate is determined by the diameter of the dispense tip, its length, viscosity of gasket material and the pressure applied to the reservoir. The gasket material is transferred from its container to a syringe barrel. The dispense tip end is capped closed and the syringe is centrifuged to eliminate air pockets in the column of gasket material in the syringe. Air gaps in the gasket material inside the syringe cause problems during dispensing. First, if an air gap reaches the dispense tip, this disrupts the flow of gasket material and causes defects in the gasket as it is forming. Second, air gaps are compressible and they will cause a change in flow rate (also called feed rate) of the gasket material. After the centrifugation, a plunger is placed in the syringe barrel and pushed until it contacts the gasket material. The cap at the dispense end of the syringe is removed and a dispense tip is attached. The syringe is placed on the dispense system and attached to the pressure source. The pressure regulator is set to the proper dispense pressure for the application. Pressure is applied to the syringe to prime the dispense tip. The pressure is kept on until a steady stream of gasket material is being dispensed. One could collect the gasket for a set time and weigh it to check the feed rate. The pressure is adjusted for proper feed rate. In most cases, the dispense syringe and tip are disposable and as a result are usually at a different height and position with respect to the dispense system. Using the calibration tools, the tip position is measured and adjusted.

Each type of gasket, shape, height and part has a different program on the computer controlled dispensing system. The proper program is loaded from the computer to the operating software. The substrate is held in place so as to have a reference position on the dispense system. In addition, the dispense system can reference to the substrate using an optical measurement system such as a camera to adjust for parts that vary slightly. A convenient hold down mechanism is vacuum fixture. While the vacuum is off, the substrate is placed in position on the fixture. The vacuum is turned on and then held in place. After the substrate is in place and secure, a test run is performed. After the test run, the substrate is evaluated for correctness. This is usually a visual inspection to ensure a complete gasket and that the shape and profile are correct within limits determined by the application. One or more test runs can be performed for this evaluation. If corrections are needed, one or more of the parameters are adjusted. Usually, if the calibration is done correctly for the dispense tip position and the feed rate of the gasket material is within proper range, no further adjustments are required. The process is now ready to start producing large numbers of gaskets. To ensure consistent gaskets, monitoring for gasket shape and height is required. The feed rate can also be monitored after a set number of parts have been fabricated to check for changes. Again, adjustments can be made for any changes.

Figure 8:
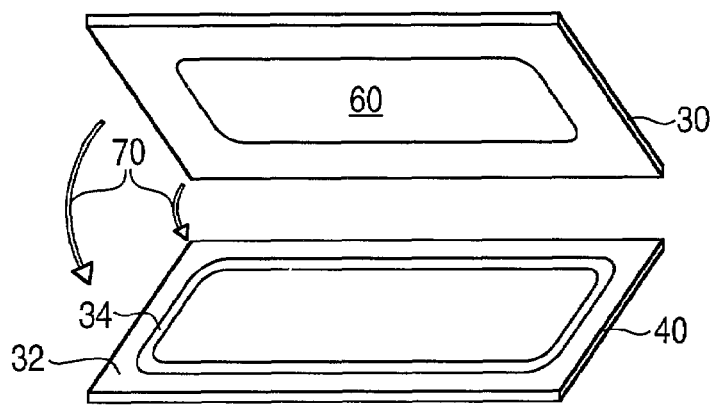
FIG. 8 illustrates a form-in-place gasket on a cover forming a well suitable for holding an aliquot of sample fluid, with the array substrate ready to be positioned on the form-in-place gasket.

Preparing Sample for Array Hybridization:

The form-in-place gasket can be used with any kind of reaction that can be adapted to use chambers such as those described herein. Oligonucleotide arrays and protein arrays are specific applications in which a chamber includes or encloses a "probe", otherwise known as a capture agent, attached to a surface, such as glass. The form-in-place gasket can be on the array glass or on the cover that creates the other half of the chamber. In this example, illustrated in FIG. 8, a cover 40 has a gasket surface 32 with a form-in-place gasket 34 formed on the gasket surface. The cover 40 with the form-in-place gasket 34 forms a shallow well that can hold an aliquot of fluid, e.g. of the target sample. The cover 40 is adapted to having the array substrate 30 placed over the cover 40 (following arrows 70), thus forming an assay chamber in which the array 60 may be contacted the fluid in the assay chamber. The thickness of the form-in-place gasket can be varied depending on system and experimental design. The layout, size and thickness of the form-in-place gasket depends on the volume of sample desired and the particular application.

Specifically, an 8500 feature array with single stranded oligonucleotide probes was used. Conditions for hybridization assays are well known in the literature and can be adapted by one of ordinary skill in the art to meet the design considerations of the particular assay used. In this example, the following components were placed in a 1.5 mL nuclease-free microcentrifuge tube: 1.25 µg cyanine 3-labeled linearly amplified cRNA, 1.25 µg cyanine 5-labeled linearly amplified cRNA, and 25 µL 10× Control Targets. Control targets are complementary targets that are spiked (added) at a known concentration; the probes for the control targets are usually on the border of the array—these spots help the analysis software find the borders. Then, nuclease-free water was added to make a volume of 125 µL. Then, 2× hybridization buffer (150 mM LiMES (pH 6.1), 612 mM LiCl; 1.0% octylphenol ethylene oxide condensate (tradename Triton X-100®), 1.5% lithium lauryl sulfate, 6 mM EDTA) was added to bring the volume to 250 µL. This is what was used as the target sample. The target sample was vortexed briefly to mix it, and then the sample was spun down in a microcentrifuge. It will be appreciated that other volumes of target sample can be used as well, and that such variations in system and experimental design lie within ordinary skill.

Loading the Sample onto a Form in Place Gasket and Hybridizing:

In order to load the biological sample, the cover with the form-in-place gasket was placed on the work bench. The target sample was placed, either by pipetting or by some other means, into the well formed by the gasket on the cover. The array substrate was placed over the cover with the active (array) side down, so that the array would interact with the target sample (as indicated by the arrows 70 in FIG. 8). The assembly was clamped together so that it was secure in the assembly clamp. The assay chamber assembly (array substrate plus gasket/cover plus target sample) was placed on the rotator rack in the hybridization oven (oven with rotating rack mechanism is from Robbins Scientific, Sunnyvale, Calif.), at 60° C. Each assay chamber assembly was clamped on its side and was rotated end-over-end on the rotator rack to achieve mixing/stirring of the target sample in the assay chamber. The hybridization rotator rack was set to rotate at about 4 rpm. Other assay chamber assemblies were similarly prepared and placed in the rotator rack. The hybridization was conducted at 60° C. for 17 hours. In accordance with the invention, the conventional hybridization solutions and processes for hybridization can be used, such as those described in Sambrook et al., Molecular Cloning: A Laboratory Manual, Cold Spring Harbor Laboratory Press, Cold Spring Harbor, Ed. 2nd, 1989, vol. 1-3, incorporated herein by reference. Conditions for hybridization typically include (1) high ionic strength solution, (2) at a controlled temperature, and (3) in the presence of carrier DNA and detergents and divalent cation chelators, all of which are well known in the art. Increased stringency is achieved by elevating the temperature, increasing the ratio of co-solvents, lowering the salt concentration, and the like.

The form-in-place gasket can also be used at most temperatures up to the highest specified temperature of the gasket material. The gasket also holds a seal in a centrifugal field, and may be used with a rotator which acts as a centrifuge to impart a centrifugal force to enhance mixing in the assay chamber. Different rotating speeds can be used. In certain embodiments, no rotation may be needed or used. This example describes loading the sample manually (via pipetting), but the assay chamber incorporating the form-in-place gasket is also amenable to automation.

Disassembly, Washing, Drying and Scanning the Array:

Before the incubation was finished, three staining dishes were prepared. Each held about 250 mL of solution. Wash Solution 1 (6×SSC, 0.005% Triton X-102) at 60° C. and a slide rack were placed in the first staining dish. Wash Solution 1 (at room temperature, enough to cover a slide rack) and a magnetic stir bar were added to the second dish. The third dish was placed into a container filled with ice (a Pyrex loaf pan is well-suited to this purpose). A magnetic stir bar and enough Wash Solution 2 (0.1×SSC, 0.005% Triton X-102) at 4° C. to cover a slide rack were placed into the third staining dish. The ice in the outer container was replenished as needed to keep the solution as cold as possible. A single assay chamber assembly was removed from the oven and inspected to determine if bubbles formed during hybridization, and if all bubbles were rotating freely. The cover, with the gasket, and the array substrate were removed from the assembly clamp but kept together, making sure the fluid did not leak out.

The two slides were placed in the slide rack in the first staining dish, which is filled with 60° C. Wash Solution 1. The assay chambers were disassembled by separating the slides while they were immersed in solution. A thin object slid between the slide and cover aided in separating the two pieces of glass. Disassembly of the chamber while immersed provides an advantage of quickly diluting the sample fluid, resulting in lower background signal. The cover (with the gasket) was removed from the slide rack and put aside. These steps were repeated for all remaining assay chamber assemblies. The slide rack with the arrays was quickly transferred to the second staining dish (Wash Solution 1 at room temperature) and set over a magnetic stir plate to stir at medium speed. The slides were washed for 10 minutes at room temperature. The slide rack was then transferred to the third staining dish, which is on ice. The dish was placed on a magnetic stirring plate set to medium speed. The slides were washed for 5 minutes at 0 to 4° C. Then the slide rack was removed from dish and placed directly into a centrifuge to dry the slides at 1000 RPM for 3 minutes. The slides were loaded into a scanner, and fluorescence intensities were measured. Any effective method of array interrogation may be used, including various methods known to those of skill in the art. After scanning, slides were stored in polypropylene slide boxes without cork or foam inserts, in a vacuum desiccator or a nitrogen purge box, in the dark.

The above example describes the process of using the form-in-place gasket in forming an assay chamber for array hybridization. It replaces two prior different prior hybridization technologies—the "large volume hybridization method" and the "coverslip" method. The large volume hybridization method required assembling a chamber that consisted of a molded plastic backing part with holes that septa fit into. The arrays were placed into a stainless steel holder then the plastic backing was placed on top. A rubber, square, O-ring was fit on top of the plastic backing to give it some compliance. Then the top of the stainless steel chamber was placed on the O-ring. The two stainless steel assembly parts were secured together with 6 screws. These screws had to be tightened down with a screwdriver. Then the two septa per array were inserted into the holes in the plastic molded backing part. After assembly of the assay chamber, the sample still had to be inserted into the assay chamber, where it would contact the array. This was done by placing a syringe needle into one septum to vent the chamber while the syringe needle with the sample was placed into the other septum and the sample was injected.

The other prior method of array hybridization used the "coverslip." In this method the scientist placed the array on the work bench, pipettes the sample onto the array and then places a coverslip on top. This method is highly error prone, since the coverslip can move around easily because it just "floats" over the sample solution. The results from coverslip hybridizations were also very unrepeatable since coverslips bent easily and bowed. This non-uniformity caused different parts of the array to have different signals because of the varying height of the sample above each part of the array. Also, during the relatively warm temperatures used for the hybridization experiments, the sample solution would evaporate from around the edge of the coverslip, adding to the non-repeatability of the results.

The form-in-place gasket as described herein removes the need for non-compliant molded parts, syringes, septa and the use of the screw driver. It also eliminates problems associated with the coverslip method.

Multiple Array Format:

The invention also provides for the use of form-in-place gasket fabrication to construct a multiple array substrate wherein arrays on a single substrate are separated by form-in-place gaskets resulting in one (or more) arrays per assay chamber (also called "assay channel", in this example). A series of arrays are prepared using a standard 1×3 inch microscope slide as the array substrate. The arrays are disposed on the array substrate on 4.5 mm centers. Multiple assay channels are constructed by applying beads of silicone gasket material from one edge of the slide to the other along the short dimension of the array substrate. The layout of such a slide is as shown in FIG. 5. After the silicone gasket material is applied to the array substrate, another glass slide (the cover) is placed on top, and the silicone is allowed to cure. Assay chambers ("assay channels") are thus formed in the space between the array substrate and the cover and between the beads of silicone. Depending on the choice of silicone gasket material, the thickness of the gasket ("height" of the assay chamber) may range from about 25 micrometers to about 200 micrometers. Given this range, the volume for the above type of assay chamber is about 2 to about 15 microliters. Other volumes are possible by varying the design, as should be apparent.

Sample integrity is maintained by an air gap channel (feature 66 in FIG. 5) between each assay chamber. If sample leaks around the inlet, the outlet, or past a gasket forming the assay chamber, it is drawn into the adjacent air gap channel. If the sample is not completely drawn into the capillary (assay channel) and excess remains at the opening, any excess wider than the opening is drawn into the adjacent air gap channel.

The multiple array substrate with the cover in place forms a multi-channel microarray. An additional feature can be added: at the openings (the inlets and outlets, or ports) on the edge between the two glass slides—another bead of silicone can be dispensed to form a gasket. This additional gasket is oriented on a plane that is not coincident with the substrate and can define further liquid handling structures, e.g. an interface port. The additional gasket disposed on the edge of the multi-channel microarray (the interface port) can then be used as a make and break seal (a reusable seal) for operations such as sample introduction, mixing, and washing. Such operations would be conducted at one or more "stations", or fluid handling devices adapted to interface with the multi-channel microarrays. Such stations may be constructed by those of skill in the art given the description herein of multi-channel microarrays. By having the gasket on the disposable multi-channel microarrays instead of the station, cross contamination between experiments will be minimized.

Filling the Chamber with Sample:

In one example, the assay chamber, formed with the silicone beads between the array substrate and the cover, is approximately 50 microns in height. This assay chamber is essentially a capillary, and the liquid sample will be drawn into the capillary. Several techniques can be employed to apply the sample to the opening (the inlet) on the end of the sandwiched slides. First, is a manual technique. Sample is aspirated into a disposable pipette, then the tip is place at the opening and the sample slowly dispensed as the capillary is filled.

Second, a flexible bottom microtiter plate can present a drop to the opening of the capillary (the inlet) and the sample will be drawn into the channel. A multi-channel pipette can perform this operation in parallel. The automation of the operations is possible if the channels are at a standard microtiter plate spacing. That would be 9 mm for a 96 well plate, 4.5 mm for a 384 well plate, and 2.25 mm for a 1536 well plate. Other possibilities include pumping the sample into the capillary or sucking the sample into the capillary by a vacuum applied to the opposite side (the outlet).

Hybridization:

After the sample in a hybridization buffer has been drawn into the channel, a standard hybridization can be performed. The multi-channel microarray can be placed in a humid chamber at the appropriate temperature. Evaporation is controlled by the humid environment. This is similar to the cover slip hybridization procedure used now.

Mixing:

The sample can be mixed on the array during hybridization by alternating pressure and vacuum on the opening of the capillary pumping the liquid back and forth across the array. Flow channels and/or mixing chambers and or mixing structures may advantageously be incorporated into the design of the device.

Washing:

Washing may be accomplished by exchanging the sample/hybridization solution with wash buffer. This can be automated with the multi-channel microarray by mating the openings with a wash station and having the wash solution either pumped into or drawn into the channel. The temperature of the wash solution can also be controlled. In manual procedures, many array substrates are placed in the same wash buffer. This can cause cross contamination. By having each channel perform the wash operation independently, cross contamination is minimized/eliminated.

Drying:

After washing, the wash buffer must be removed from the array and dried. This can also be automated by mating the openings with a drying station and either pressurizing the chamber with $N_2$ or by vacuum on the outlet side.

Automation of Entire Process:

Because the channels are at the spacing of a standard micro titer plate, automation of a complete microtiter plate's worth (or even many plates' worth) of samples is possible. For example, a rack of multi-channel microarrays can be set up for analysis of one or more microtiter plates containing samples. For each microtiter plate (e.g. a 96 well plate), there could be, e.g. twelve multi-channel microarrays with eight channels per substrate that would match the spacing of the samples in the corresponding plate. The automated machinery would pick up a substrate, apply samples from a row in the microtiter plate, and continue with the hybridization process.

By providing spacing of the channels that is compatible with microtiter plates, the multiple array format allows automation for sample preparation prior to hybridization. All of the sample prep including isolation, amplification, labeling can be done in microtiter plates and then interfaced with the multiple array format for hybridization and washing.

As described in this example, the processes and devices according the present invention may provide one or more of the advantages described herein, including the following: existing array manufacturing processes may be easily adapted for use with form-in-place gasket techniques; multiple array formats are easily provided (as compared to current approaches only using one or two arrays per substrate or larger substrates cut into smaller pieces with one array per piece); easy conversion to automation of sample introduction, hybridization, and washing; interfacing with standard microtiter plate automation equipment; scales to batch automation from a single substrate to large scale at microtiter plate increments (e.g 8, 12, 16, 24, 96, 384, 1536).

The invention thus provides for an assay chamber. The assay chamber includes a substrate that has a gasket surface with a form-in-place gasket on the gasket surface. The assay chamber also includes a cover having a mating surface that is complementary to the gasket surface and that can be placed adjacent the substrate with the mating surface against the form-in-place gasket to form a fluid tight seal. Essentially similar alternate configurations are possible, e.g. in which the gasket surface is on the cover and the mating surface is on the substrate. The assay chamber typically includes at least one analysis component (e.g. an array of immobilized oligonucleotides) necessary for performing, e.g. a biochemical assay, such as a binding reaction between an immobilized oligonucleotide and a complementary oligonucleotide in the sample solution.

The invention provides a method of performing a hybridization assay using an assay chamber that includes a form-in-place gasket. In one embodiment the method includes mating a cover against a complementary surface on a substrate, wherein the substrate has an array surface on which biomolecules are deposited in an array format. A form-in-place gasket is present on the cover, and when the cover is mated against the complementary surface a assay chamber is formed. The method may further include contacting the array surface with the solution to be tested, disassembling the chamber by removing the cover, processing the array surface, and interrogating the array surface using, e.g. an array reader. In alternate embodiments no disassembly is required, because the assay chamber is adapted to allow interrogation of the array surface without disassembly, e.g the cover may have a transparent area allowing light from the array reader to reach the array surface. In some embodiments, other configurations of assay chamber may be used, e.g. the form-in-place gasket may be present on the substrate surface and mated against a complementary surface on the cover, or the array surface may form a portion of a separate array substrate that is held in place between the substrate and the cover.

The invention provides for a multiple array substrate having form-in-place gaskets defining assay chambers around one or more arrays. Each assay chamber is in fluid communication with a port, and the ports are positioned in a spatial format adapted to interface to standard laboratory equipment for handling multiple fluids in parallel. Particular embodiments have either eight or twelve assay chambers, each in fluid communication with a port, the ports linearly positioned on 9 mm centers. Other embodiments have either sixteen or twenty-four assay chambers, each in fluid communication with a port, the ports linearly positioned on 4.5 mm centers. Other embodiments have either thirty-two or forty-eight assay chambers, each in fluid communication with a port, the ports linearly positioned on 2.25 mm centers. Such a configuration allows for automated handling of processing of arrays, including contacting arrays with the solutions to be tested, washing buffers, etc.

The form-in-place gaskets of the current invention may be quite thin because the form-in-place gaskets do not have to be handled or positioned in order to get the gasket properly positioned on the intended surface (because the gasket is formed on the surface). This minimizes problems of alignment, damage, and contamination that arose in previous methods of applying pre-formed gaskets to surfaces. Earlier methods that use pre-formed gaskets require handling and positioning of gaskets on the site where a fluid tight seal is desired. Problems with the earlier methods arose when a very thin gasket was desired—handling and positioning very thin, pliable gaskets is difficult because the thinness makes the gasket delicate and easily damaged. The method provided herein is thus an advantageous solution to the noted problems. Where very small volumes of solution are desired in a biochemical assay, the thin, form-in-place gaskets described herein are advantageous for providing biochemical assay chambers that are thin and as a consequence require only very small volumes of solution. While allowing a small sample volume to be used for the biochemical assay, the form-in-place gasket keeps the substrate surface from coming into direct contact with the surface of the cover. This can be beneficial where the analysis component is located on the substrate surface and can be damaged by inadvertent contact with the cover.

The gasket material is typically deposited on a substrate and then is cured to form a fluid tight seal between the gasket material and the substrate surface. Prior methods of forming fluid tight seals using preformed gaskets typically require relatively thick gaskets and result in a need to make a fluid tight seal between the cured gasket and the substrate and also between the cured gasket and the cover. In contrast, the present method results in a fluid tight seal between the gasket material and the gasket surface as the gasket material is curing. This leaves only one fluid tight seal, between the cured form-in-place gasket and the mating surface on the cover, to be made upon placing the cover on the gasket. The cross section, or profile, of the form-in-place gasket may be dome-shaped, or rounded. A dome-shaped profile provides for point contact with the mating surface of the cover, resulting in lower compressing forces needed to form a fluid tight seal.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A structure comprising a plurality of form-in-place gaskets that are spaced at uniform intervals to form a plurality of fluid containment structures, wherein each fluid containment structure includes an inlet and an outlet through the form-in-place gasket in a plane parallel a substrate and a cover and not through the substrate and the cover, wherein the inlet and the outlet are disposed on opposite ends of the containment structure, wherein each of the fluid containment structures are in fluid communication with an external fluid dispensing system via the inlet of each containment structure, wherein each form-in-place gasket is disposed on the substrate, wherein each form-in-place gasket forms a permanent seal between the form-in-place gasket and the cover, wherein the form-in-place gasket and the substrate define each fluid containment structure, wherein each fluid containment structure is contained on the top by the cover, wherein each fluid containment structure is contained on the side by the form-in-place gasket, wherein each fluid containment structure is contained on the bottom by the substrate, wherein each fluid containment structure is in operable association with an array, wherein the form-in-place gaskets consist of gasket materials selected from at least the following: silicon sealants, urethane, polysulfide, latex, and acrylic sealants, and wherein the cover and the substrate are made of different materials than the form-in-place gasket.

2. The structure of claim 1, wherein the form-in-place gaskets are between about 10 micrometers and about 250 micrometers thick.

3. The structure of claim 1, wherein the form-in-place gaskets are between about 250 micrometers and about 1.5 millimeters thick.

4. The structure of claim 1, wherein the form-in-place gaskets are between about 100 micrometers and about 3 millimeters wide.

5. The structure of claim 1, further comprising an analysis component in operable relation to the substrate.

6. The structure of claim 1, wherein the uniform interval is selected from the group consisting of about 4.5 mm, about 9 mm, and about 2.25 mm.

7. The structure of claim 1, further comprising:
 a first fluid containment structure and a second fluid containment structure, wherein an outlet of the first fluid containment structure is in fluid communication with an inlet of the second fluid containment structure via a channel, and wherein the first fluid containment structure and the second fluid containment structure are positioned in series with one another.

8. The structure of claim 7, wherein the uniform interval is selected from the group consisting of about 4.5 mm, about 9 mm, and about 2.25 mm.

9. The structure of claim 1, wherein the form-in-place gaskets are between about 10 micrometers and about 100 micrometers thick.

10. The structure of claim 1, wherein the form-in-place gaskets are between about 10 micrometers and about 50 micrometers thick.

11. A method of forming a fluid containment structure comprising
 depositing a gasket material onto a substrate,
 curing the gasket material to provide a plurality of form-in-place gaskets to form a plurality of fluid containment structures, wherein each form-in-place gasket defines an interior area of the substrate, and the interior area and the form-in-place gasket together define each fluid containment structure and a plurality of inlets and outlets, wherein each fluid containment structure is in fluid communication with an inlet and an outlet, wherein each inlet and outlet are through the form-in-place gasket in a plane parallel the substrate and a cover and not through the substrate and the cover, wherein the inlet and the outlet are disposed on opposite ends of the fluid containment structure, wherein each form-in-place gasket forms a permanent seal between the form-in-place gasket and a cover, wherein each fluid containment structure is contained on the top by the cover, wherein each fluid containment structure is contained on the side by the form-in-place gasket, wherein each fluid containment structure is contained on the bottom by the substrate, wherein the fluid containment structure is in operable association with an array,
wherein the form-in-place gaskets consist of gasket materials selected from at least the following: silicon sealants, urethane, polysulfide, latex, and acrylic sealants, and wherein the cover and the substrate are made of different materials than the form-in-place gasket.

12. The method of claim 11, wherein the gasket material is self leveling.

13. The method of claim 11, wherein the gasket material is non-slumping.

14. The method of claim 11, wherein the form-in-place gasket is of uniform thickness.

15. The method of claim 11, wherein the form-in-place gaskets are between about 10 micrometers and about 250 micrometers thick.

16. The method of claim 11, wherein the form-in-place gaskets are between about 250 micrometers and about 1500 micrometers thick.

17. The method of claim 11, wherein the form-in-place gaskets are between about 100 micrometers and about 1000 micrometers wide.

18. The method of claim 11, wherein the form-in-place gaskets are between about 100 micrometers and about 3000 micrometers wide.

19. The method of claim 11, wherein the gasket material is a self-leveling material that has a viscosity of between about 15,000 to about 50,000 centipoise.

20. The method of claim 11, wherein curing comprises a process selected from the group comprising contacting the gasket material with moisture in the air, heating the gasket material, shining light on the gasket material, and contacting the gasket material with a catalyst.

21. The method of claim 11, wherein the substrate further comprises an analysis component.

22. The method of claim 11, wherein the fluid containment structures are spaced at a uniform interval that is selected from the group consisting of about 4.5 mm, about 9 mm, and about 2.25 mm.

23. The method of claim 11, further comprising:
forming a first fluid containment structure and a second fluid containment structure, wherein an outlet of the first fluid containment structure is in fluid communication with an inlet of the second fluid containment structure via a channel, and wherein the first fluid containment structure and the second fluid containment structure are positioned in series with one another.

24. The method of claim 23, wherein the first fluid containment structure and the second fluid containment structure are spaced apart by a uniform interval that is selected from the group consisting of about 4.5 mm, about 9 mm, and about 2.25 mm.

* * * * *